United States Patent [19]

Korth

[11] Patent Number: 5,605,927
[45] Date of Patent: Feb. 25, 1997

[54] TREATMENT OF SKIN DISEASES USING GINKGOLIDE PAF ANTAGONISTS

[75] Inventor: Ruth Korth, Palestrinastr. 7A, D-80639, Munich, Germany

[73] Assignee: Ruth Korth, Munich, Germany

[21] Appl. No.: 261,765

[22] Filed: Jun. 17, 1994

Related U.S. Application Data

[63] Continuation of Ser. No. 969,674, Oct. 28, 1992, Pat. No. 5,346,894, which is a continuation-in-part of Ser. No. 246,476, May 19, 1994, abandoned.

[30] Foreign Application Priority Data

Nov. 4, 1991 [EP] European Pat. Off. ............... 91118745

[51] Int. Cl.$^6$ ..................................................... A61K 31/35
[52] U.S. Cl. ............................ 514/453; 514/844; 514/864
[58] Field of Search ................................................. 514/453

[56] References Cited

U.S. PATENT DOCUMENTS

| | | | |
|---|---|---|---|
| 4,571,407 | 2/1986 | Chatterjee et al. | 514/464 |
| 4,595,693 | 6/1986 | Biftu et al. | 514/461 |
| 4,734,280 | 3/1988 | Braquet | 425/195.1 |
| 5,147,864 | 9/1992 | Wissner et al. | 514/82 |
| 5,202,313 | 4/1993 | Bombardelli et al. | 514/100 |
| 5,334,592 | 8/1994 | Billah | 514/220 |

FOREIGN PATENT DOCUMENTS

| | | |
|---|---|---|
| 0256687A1 | 2/1988 | European Pat. Off. . |
| 0312913B1 | 4/1989 | European Pat. Off. . |
| 0459432A1 | 12/1991 | European Pat. Off. . |
| 8716044 U | 8/1992 | Germany . |
| 42 44 265.6 | 12/1992 | Germany . |

OTHER PUBLICATIONS

Meade et al., Biochem. Pharm, vol. 41, No. 5 (1991) 657–668, "Biochemical Pharmacology of Platelet–Activating Factor (and Paf Antagonists) in Relation to Clinical and Experimental Thrombocytopenia".

Goldman et al., New Engl. J. Med., vol. 318, No. 7, (1990) 397–403 "Mechanisms of Altered Water Metabolism in Psychotic Patients with Polydipsia and Hyponatremia".

Yue et al., Am. Soc. Pharmacol. and Exp. Ther., vol. 257 (1991) 374–381 "Platelet–Activating Factor (PAF) Receptor–Mediated Calcium Mobilization and Phosphoinositude Turnover in Neurohybrid NG108–15 Cells: Studies with BN50739, a New PAF Antagonist".

Pfeilschifter et al., Eur. J. Biochem, 181 (1989) 237–242, "Release of phospholipase $A_2$ activity from rat vascular smooth muscle cells mediated by cAMP".

Tetta et al., J. Pharmacol. and Exp. Ther., vol. 257 (1990) 616–620 "Inhibition of the Synthesis of Platelet–Activating Factor by Anti–Inflammatory Peptides (Antiflammins) Without Methionine".

Lekka et al., Biochimica et Biophysica Acta, 1042 (1990) 217–220, "In vivo metabolism of platelet–activating–factor (1–O–alkyl–2–acetyl–sn–glycero–3–phosphocholine) by the protozoan Tetrahymena pyriformis".

Benveniste et al., J. of Exp. Med., 136 (1972) 1356–1377, "Leukocyte–Dependent Histamine Release from Rabbit Platelets".

Korth et al., Eur. J. Pharmacology, 152 (1988) 101–110, "Comparison of three paf–acether receptor antagonist ginkgolides".

Korth et al., Br. J. Pharmacol., 98 (1989) 653–661, "Interaction of the Paf antagonist WEB 2086 and its hetrazepine analogues with human platelets and endothelial cells".

Malech et al., New Engl. J. Med., vol. 317, No. 11, (1987) 687–694 "Current Concepts: Immunology—Neutrophils in Human Diseases".

Sperling et al., J. Immunol., 139 (1987) 4186–4191, "The Effects of N–3 Polyunsaturated Fatty Acids on the Generation of Platelet–Activating Factor–Acether by Human Monocytes".

Llorens–Cortes et al., J. Biological Chem., 267 (1992) 14012–14018 "Identification and Characterization of Neural Endopeptidase in Endothelial Cells from Venous or Arterial Origins".

Benveniste et al., C. R. Acad. Sc. Paris, 289 (1979) 1037–1377 "Semi–synthèse et structure proposée du facteur activant les plaquettes (P.A.F.): PAF–acether, un alkyl ether analogue de la lysophosphatidylcholine".

Korth et al., Lipids, vol. 28, No. 3 (1993) 193–199, "Human Platelets Release a Paf–Acether: Acetylhydrolase Similar to That in Plasma".

Honda et al., Nature, vol. 349 (1991) 342–346), "Cloning by functional expression of platelet–activating factor receptor from guinea–pig lung".

Primary Examiner—Theodore J. Criares
Attorney, Agent, or Firm—Nikaido, Marmelstein, Murray and Oram LLP

[57] ABSTRACT

The invention refers to the treatment and prevention of lyso paf-mediated skin disorders with an effective amount of at least one antagonists against lyso paf receptors. Lyso paf or paf receptor antagonists were administered with or without an antagonist against production of ether phospholipids. Lyso paf antagonists are Ginkgoloides which are administered, for example, by food or topically.

3 Claims, No Drawings

TREATMENT OF SKIN DISEASES USING GINKGOLIDE PAF ANTAGONISTS

This application is a Continuation-In-Part of U.S. application Ser. No. 07/969,674, filed Oct. 28, 1992, now U.S. Pat. No. 5,346,894, and Ser. No. 08/246,476, filed May. 19, 1994, now abandoned.

Lyso paf receptors on leukocytes

The invention refers to the treatment and prevention of diseases with antagonists directed against lyso paf and a procedure for determining the efficacy of such antagonists. The invention refers also to the treatment and prevention of leukocyte-mediated disorders. A combination of antagonists against enhanced binding and turnover of ether phospholipids is suitable for therapeutics and for a procedure for determining the efficacy.

According to the invention, lyso paf is a phospholipid with a biologically active ether group in the position 1 of the molecule. Here we show, for the first time, a specific lyso paf receptor on neutrophils interacting specifically with the ether group. The lyso paf receptor on intact human neutrophils is functionally relevant as it up-regulates neutrophil paf receptors. Lyso paf has the chemical structure 1-O-alkyl-sn-glycero-3-phosphocholine with an ether alkyl group in position 1 being, for example, hexadecyl or octadecyl. Lyso paf is formed via deacetylation of paf by a specific acetylhydrolase, or from alkyl-acyl-glycero-phosphocholine by phospholipase $A_2$ activity. Lyso paf is generally considered an ineffective precursor/metabolite of the platelet activating factor (paf) because it does not activate platelets. The shown data have clinical relevance as lyso paf was found here in the indicated disorders.

According to the invention, lyso paf activates neutrophils via up-regulatory lyso paf binding sites on the surface of intact human neutrophils. Lyso paf is formed by endothelial cells to facilitate the adherence and/or emigration of blood cells such as neutrophils and eosinophils some hours later. Lyso paf interferes with bacterial phagocytosis because paf is metabolized with intermediary of lyso paf to alkyl-acyl-glycero-phosphocholine in lower eucaryotes such as Tetrahymena pyriformis [Lekka et al. Biochim. Biophys. Acta 1042:211 (1990)]. Lyso paf is formed also by lipoproteins, leukocytes and platelets which release enzymes which can produce lyso paf.

Paf (formerly "Paf-Acether", platelet activating factor) is also an ether phospholipid chemically defined as 1-O-alkyl-2-acetyl-sn-glycero-3-phosphocholine. The stereoisomeric configuration of the acetyl group in the position 2 of the molecule (not the ether group) interacts with paf receptors resulting beside other effects, in a cytosolic $Ca^{2+}$ rise to activate cells. Paf has been originally described as a mediator of the acute phase of allergic diseases, because it is released by IgE-sensitized basophils [Benveniste et al., J. Exp. Med. 136:1356 (1972)]. Paf activates various blood cells via specific paf receptors. Specific paf receptor antagonists are, for example, ginkgolides (plant extracts from Ginkgo biloba), hetrazepines such as WEB 2086 and paf analogues as they inhibit paf-mediated cell activation. The chemical terms are given on page 7 [Korth et al., Eur. J. Pharm. 152:101, (1988); Korth et al., 98:653 (1989); Korth, Eur. patent applications 0 312 913 and 91108763.3].

The binding of chemotactic factors to neutrophil surface receptors leads to chemotactic and chemokinetic migration, adherence, degranulation and production of superoxide anions [for review, Malech and Gallin, New Engl. J. Med., 317:687 (1987)]. Paf is also a potent chemotactic factor for human eosinophils, regulates IgE binding to normal density eosinophils, superoxide formation and eosinophil degranulation and adherence to endothelial cells with emigration [for review Meade et al., Biochem. Pharm. 41:657 (1991)]. Leukocytes such as neutrophils and eosinophils are involved in various inflammatory reactions such as allergy, cell migration and phagocytosis, aging, irritation and degeneration of cells. Thus, mechanisms regulating leukocyte receptors are of clinical interest.

According to the invention, the ether group of lyso paf interacts with the specific lyso paf receptor on intact neutrophils and up-regulates lyso paf and paf receptors. The acetyl group in paf (not lyso paf) mediates calcium flux. The acetyl group in paf down-regulates paf receptors on eosinophils. Thus, it is possible that in certain clinical cases, in vivo exposure of neutrophils to submaximal concentrations of ether phospholipids leads to up-regulation of their paf and lyso paf receptors whereas exposure of eosinophils to low dose paf (not lyso paf) leads to down-regulation of eosinophil paf receptors leading to inefficiency of known paf receptor antagonists. These phenomena might be causatively involved in the onset of inflammatory, allergic, sclerotic reactions characterized preferably by leukocytes.

Our invention describes, quite surprisingly, lyso paf binding sites on neutrophils (not eosinophils) which were functionally relevant as they mediated paf receptor up-regulation. These lyso paf binding sites are not identical with paf binding sites because: 1) an excess of unlabeled paf did not prevent but increased [$^3$H]lyso paf binding, 2) known paf receptor antagonists such as WEB 2086 were inefficient and 3) lyso paf failed to mediate $[Ca^{2+}]$ rise in neutrophils and this was contradictory to a full $[Ca^{2+}]$ rise in response to paf. We showed here that lyso paf binding sites interact specifically with the ether group of lyso paf. Ether phospholipids together showed no additive effects and the ester group in 2-lyso phosphocholine (LPC) was inefficient. In addition, up-regulatory effects of ether compounds interfered with direct stimulation of the protein kinase C (PKC) in response to submaximal dose of phorbol-12-myristate-13-acetate (PMA). Thus, a nonspecific detergent-like property of lysophospholipids did not interfere with neutrophils. According to our invention, lyso paf can be considered now as an active mediator.

According to the invention, it has now been discovered that lyso paf (not paf) is present in the cerebrospinal fluids of patients with psychiatric symptoms. Quite surprisingly, lyso paf, but not paf, was found in patients with mental, neuronal, sclerotic, degenerative, genetic or inflammatory disorders. Lyso paf, preferably in the body fluids, activates leukocytes and/or neuronal cells. It is also possible that the increased amount of lyso paf in the body fluids leads to an increased emigration of leukocytes with consequent disturbance of the blood brain barrier. Since the endothelium provides protection of the brain, various mediators or oedema might then attack the central nervous system. For example, water intoxication has been shown to be a serious problem in many patients with chronic psychiatric illness [Goldman et al., New Engl. J. Med. 318, pp. 397–403, (1990)]. Psychiatric patients with polydipsia and hyponatremia have unexplained defects in urinary dilution, osmoregulation of water intake and secretion of vasopressin. Dopamine secretion may provide a link between psychosis and vasopressin secretion.

According to the invention, it is suitable to prevent or treat mental or neuronal disorders, for example, psychosis, aging or multiple sclerosis using antagonists directed against lyso paf. These antagonists can be administered to avoid episodic defects in osmoregulation of water intake with diverse neurological and mental symptoms. For example, ginkgolides are administered. The administration with food, for example, with "FIDA-infants' foods for invalids and seniors" is preferably suitable for older persons, for children and psychiatric patients.

Lyso paf and/or paf receptor antagonist

According to the invention, lyso paf antagonists are called here "Ginkgoloides" as they are directed against lyso paf receptors and/or against metabolism of ether phospholipids. Up to now, specific lyso paf antagonists are not known. According to the invention, they should be found by the present screening procedure. Up to now, paf antagonists are neither used against lyso paf nor to treat or prevent disorders with a genetic background. In this context, it is suitable to find new lyso paf antagonists directed specifically against lyso paf receptors.

Specific paf antagonists have been described before for "treatment or prevention of paf-acether-induced maladies" [U.S. Pat. No. 4,734,280, (1988)] and "the excellent platelet activating factor antagonism" of "thiazolidin-4-one derivatives and acid additions salts thereof" with a "suppressive effect on the central nervous system" has been described in Eur. Patent Appl. No. 87306508.0 (1988). Ginkgolides specifically directed against effects of "PAF-Acether" (not lyso paf) are described [U.S. Pat. No. 4,734,280, (1988)]. Medicaments containing Bilobalid are used to treat nervous diseases with metabolic, demyelinating or toxic origin [U.S. Pat. No. 4,571,407, (1986)].

Antagonists with an effect on the central nervous system have to penetrate the blood brain barrier to protect neuronal cells or preferably protect the blood brain barrier itself. According to the invention, Ginkgoloides preferably with lipophilic character are suitable. For example, the lipophilic compound BN 50 739 (20 μM, chemical term on page 7) inhibited 5.8 fmol of the endothelial cell bound [3H]paf.

According to the invention, Ginkgoloides can be tested to antagonize lyso paf effects using lyso paf assays. Ginkgoloides are defined as being antagonists against the ether group in phospholipids. Ginkgoloides include particularly natural ginkgolides and synthetic or natural ginkgolide derivatives. Various paf antagonists have been tested. Of the ginkgolides tested, BN 52020, BN 52021 and a mixture of BN 52020, BN 52021 and BN 52022, which mixture is referred to as BN 52063, achieve the best results [Korth et al., Eur. J. Pharm. 152:101 (1988)]. The substance that inhibits leukocyte receptors in this connection can be also paf analogues, such as CV 3988. Triazolothieno-diazepines or homologous compounds should be specified with the new methods, preferably as being either specific paf receptor antagonists as shown [Korth et al., Br. J. Pharm. 98:653 (1989)]or, according to the invention, as being lyso paf antagonists. Of the triazolo-thieno-diazepine compounds, for example, hydrophilic WEB 2086 and WEB 2098 were tested. Compounds such as the lipophilic BN 50739 [Yue et al., Pharmacol. Exp. Ther. 257:374 (1991)]can also be used.

Some chemical terms are given as examples. The term of CV 3988 is rac-3-(N-n-octadecyl carbamoyl oxy)-2-methoxypropyl 2-tiazolioethyl phosphate; the term of the triazolo-thienodiazepine WEB 2086 is 3-(4-(2-chlorophenyl)-9-methyl-6H-thieno(3,2-f) (1,2,4) triazolo-(4,3-a)-(1,4) diazepine-2-yl)-1-(4-morpholinyl)-1-propanone; the term of the triazolo-thienodiazepine WEB 2098 is (3-(4-(2-chlorophenyl)-9-cyclopropyl-6H-thieno(3,2-f)-(1,2,4) triazolo-(4,3-a) (1,4) diazepine-2-yl)-1-(4-morpholinyl)-1-propanone; the term of the ginkgolide BN 52020 is 9H-1, 7a-Epoxy-methano)-1H, 6aH-cyclopenta(c)furo(2,3-b)furo(3',2': 3,4) cyclopenta (1,2-d) furan-5,9,12 (4H)-trione, 3-tert-butylhexahydro-4, 7b-dihydroxy-8-methyl; the term of the ginkgolide BN 52021 is 9H-1, 7a-Epoxymethano)-1H, 6aH-cyclopenta(c)furo(2,3-b)furo-(3',2': 3,4) cyclopenta(1,2-d)furan-5,9,12(4H)-trione, 3 tert-butyl-hexahydro-4, 4b-11-trihydroxy-8-methyl; and the term of the ginkgolide BN 52022 is 9H-1, 7a- (Epoxymethano) -1H, 6aH-cyclo-penta (c) furo (3',2': 3,4) cyclopenta (1,2-d) furan-5,9,12 (4H) -trione, 3 tert-butyl hexahydro-2,4,7b,11-tetrahydroxy-8-methyl. The chemical term of BN 50739 is tetrahydro-4,7,8,10 methyl (chloro-2 phenyl) 6 (dimethoxy-3,4-phenyl) thio)methylthiocarbonyl-9 pyrido (4',3'-4,5) thieno (3,2-f) triazolo-1,2,4 (4, 3-a) diazepine-1,4).

The antagonists directed against the ether group in phospholipids, preferably lyso paf, can be administered topically, orally, parenterally or inhalation. The compounds are administered as active ingredients in conventional pharmaceutical preparations, e.g. in compositions comprising an inert pharmaceutical vehicle and an effective dose of the active substance, such as tablets, coated tablets, capsules, lozenges, powders, solutions, suspensions, aerosols for inhalation, ointments, liposomes, emulsions, syrups, suppositories, etc. According to the invention, paf or lyso paf antagonists can also be administered as food for, example, in the form of "FIDA infants' foods for invalids and seniors" (R. Korth U.S. Trademark Appl., Ser. No. 74/416579, filing date Jul. 26, 1993).

Phospholipid production

According to the present invention, the ether group in phospholipids preferably in lyso paf modulates leukocyte receptors. Indicated diseases should be successfully treated by combination of antagonists directed specifically against ether group receptors with drugs lowering the level of ether phospholipids in blood, tissue and fluids. These compounds are suitable for treating and preventing preferably lyso paf and leukocyte-mediated mental and/or neuronal disorders as well as skin disorders. They are also suitable for inflammations, allergies with asthma, oedema for example of hepatic and nephrotic origin, bacterial, thermic, genetic, degenerative and sclerotic disorders.

According to the invention, drugs lowering the level of paf or lyso paf can be for, example, classical antiallergic and antiinflammatory drugs such as glucocorticosteroids which decrease paf and lyso paf synthesis via interaction with phospholipase $A_2$. Although antagonists of paf or lyso paf synthesis are not yet available, it is known that paf synthesis interferes with activity of the phospholipase $A_2$ via production of the paf precursor lyso paf. The activity of the phospholipase $A_2$ increases in parallel with cAMP [Pfeilschifter et al. Eur. J. Biochem., 181:237 (1989)]. Other antagonists of paf synthesis have been developed such as antiflammins [Tetta et al. J. Pharmacol. Exp. Therapeutics 257:616 (1990)]. Drugs which decrease the histamine-mediated paf synthesis are also suitable. According to the invention, antagonists against ether phospholipids are suitable to reduce side effects of antiallergic and/or antiinflammatory drugs, for example, of glucocorticosteroids. Thus, antagonists directed against ether phospholipids reduce the dose of drugs with side effects.

Lysine aspirin was not inhibitory to paf binding but quite surprisingly increased, for example, endothelial cell bound [$^3$H]paf to 177% and 198% of the total binding. This increased phospholipid binding was antagonized here, for example, by CV 3988 or WEB 2086. As paf receptors are distinct on blood cells as compared with endothelial cells (R. Korth, European Patent No. 0 312 913) various specific paf or lyso paf receptor antagonists could be added together.

It is also suitable to use phospholipid receptor antagonists, for example, with antagonists against prostaglandin synthesis such as aspirin which inhibits prostacyclin release. According to the invention, this is suitable because antagonists against ether phospholipids increase the release of prostacyclin. For example, the stable metabolite 6-keto-PGF1-alpha increased from 127±3 pg per ml to 145±11 pg per ml in the presence of 100 nM WEB 2086. BN 52021 (10 µM) increased the endothelial cell prostacyclin release from 50±2 pg per ml to 126±10 pg per ml.

Two other important groups of antiallergic and/or antiinflammatory drugs are those modulating the cellular level of cyclic adenosine monophosphate (cAMP). Xanthines, such as theophylline, or prostaglandins, such as prostacyclin, interfere directly with cAMP. Various receptor antagonist interacting, for example, with adrenergic receptors modulate cAMP. According to the invention, steroids such as cholesterol also interfere with cellular cAMP level required to differentiate cells and to express paf receptors especially on monocyte/macrophage cells.

Paf antagonists, not specifically related with paf receptors, should be prepared and tested such as: paf degrading enzymes, paf antagonizing lipids, or proteins including antibodies. According to the invention, platelets release a part of their paf degrading enzymes during aggregation. Serum albumin competes with paf effects as well as paf metabolism and protects platelets from damage. As serum albumin is reduced in hepatic, nephrotic or pancreatic disorders, paf or lyso paf antagonists seem to be suitable with or without addition of serum albumin, for example, in shock or using plasmapheresis.

Food might modulate the blood level of paf and lyso paf. Fish liver oils (N-3 polyunsaturated fatty acids) have been shown to decrease the paf synthesis in human cells [Sperling et al., J. Immunol. 139:4186 (1987)] and are commercially available now for the treatment and prevention of allergic, inflammatory and hyperlipidemic, as well as cardiovascular, diseases. As lyso paf mediates chemotaxis after its oxidation, interfering with phospholipid metabolism, antioxidative compounds such as vitamins are suitable for indicated disorders. Garlic oils are also commercially available for the prevention and treatment of allergy, inflammations and hyperlipidemic as well as cardiovascular diseases via modulation of the cAMP level.

According to the invention, skin diseases should be treated or prevented, for example, by a kit with a first container comprising antagonists against the production of ether phospholipids such as glucocorticosteroids or various antiinflammatory drugs including antibiotics as well as antiallergic drugs and a second container comprising antagonists against the effect of ether phospholipids such as Ginkgoloides. A composition could also be used comprising antagonists against production and binding of phospholipids such as glucocorticosteroids and Ginkgoloides to maintain the responsiveness of paf receptors on eosinophils. Various skin diseases such as bacterial, genetic, degenerative, inflammatory, allergic, thermic and sclerotic disorders are mediated by leukocytes. These disorders are, for example, acne vulgaris, psoriasis, neurodermitis or skin diseases after thermic damage as well as during virus diseases. Neutrophils, eosinophils, basophils, monocytes, histiocytes or lymphocytes are involved.

On the long term, however, it is suitable to develop compounds according to the invention which inhibit receptors and prevent synthesis of ether phospholipids, for example, on the cAMP level. In other words, compounds should be developed which inhibit paf or lyso paf binding and/or paf and lyso paf production, as the ether group in the position 1 of lyso paf (not the acetyl group in the SD-2 position of paf) was defined here as the active component of ether phospholipids.

Binding assays

According to the invention, antagonists were tested by new competitive binding tests in the presence of lyso paf using leukocytes, preferably polymorphonuclear neutrophils or eosinophils. Reliable information about the efficacy of lyso paf antagonists is possible in case the incubation is performed with lyso paf or by labeled lyso paf binding tests. According to the invention, cell lines or immortalized cells, for example, immortalized endothelial cells [Llorens-Cortes et al., J.Biol. Chem. 267:1402 (1992); R. Korth, German Patent Application No. P 42 44 265.6], can also be used to test the efficacy and specificity of phospholipids and/or their antagonists.

In order to conduct a quick and simple test, i.e. to use a screening procedure, antagonist activity vis-a-vis paf or lyso paf receptors was tested. For example, effective antagonists directed against different ether phospholipid receptors on leukocytes can then be considered for use in treating indicated disorders. In addition, diagnostic assays should be developed to measure lyso paf in blood, fluids or tissues. According to the invention, the best methods are to proceed as follows:

a) ether phospholipids are measured in given blood, fluids, cells or tissue;

b) cells such as leukocytes, particularly neutrophils or eosinophils, are washed with isotonic buffer;

c) a given quantity of cells is mixed with a given quantity of labeled paf or lyso paf in the presence of the antagonist to be determined;

d) a given quantity of cells is mixed with a given quantity of labeled paf or lyso paf in the absence of the antagonist to be determined;

e) the cells are separated from the mixtures c) and d) in each case;

f) the quantity of labeled paf or lyso paf bound to cells is measured in each case;

g) the efficacy of the paf or lyso paf antagonist is determined from the relationship between on the one hand the quantity of labeled paf or lyso paf which is bound to cells according to c) in the presence of the antagonist, and on the other hand the quantity of labeled paf or lyso paf which is bound to cells according to d) in the absence of the antagonist, related to the same number of cells;

h) the binding assay according to c) and d) is performed in the presence and absence of ether phospholipids; and i) the cells according to b) are washed under sterile conditions.

In accordance with step a), simple methods should be developed to measure ether phospholipids and degrading enzymes.

Preferably, eosinophils or neutrophils are used as cells for the procedure of the invention of determining the efficacy of antagonists directed against receptors for the ether group in phospholipids. In case leukocytes are used, they are washed according to the invention preferably under sterile conditions because endotoxin activates leukocytes leading to an artificial upand down-regulation of receptors. Thereafter, the purified cells are preferably dispersed in an isotonic buffer containing delipidated serum albumin, but no calcium ions. Cells are concentrated several times before they are used in steps b) and c) in the assay procedure according to claim 14 in the presence of calcium and magnesium ions. Besides blood, fluids and tissue cells, also leukocyte cultures and/or various cell lines can be used in the assay to compare binding assays with gene expression, as described for paf binding sites on blood cells by Honda et al., Nature 349:342 (1991).

As labeled ligands tritium-labeled paf, labeled LA-paf, labeled lyso paf can be used. In a modification of the assay the antagonists such as hetrazepines, paf analogues, ginkgolides or Ginkgoloides can be labeled as well. It is also possible to use labeled and unlabeled antibodies against paf or lyso paf (receptors) as well as coloured, fluorescence or spin-labeled compounds.

The mixing according to the steps c) and d) is done preferably at a temperature of 20° C. At lower temperatures, such as 4° C, up- and down-regulation cannot be detected. After mixing, the cells are incubated preferably 30 min before they are separated according to step e) of the procedure of the present invention. The separation of the cells according to step e) can be performed by filtration or centrifugation.

Next, the quantity of labeled paf or labeled lyso paf which is (specifically) bound to the cells is determined. If radioactively labeled paf is used, only the cell-bound radioactivity is measured. The radioactivity bound to filters without cells is subtracted from these values.

By drawing calibration graphs, which are obtained with varying quantities of the antagonist in accordance with step c) and d), it is possible to obtain the efficacy of the antagonist at a 50% inhibitory value, i.e. as that quantity of the antagonist which, in relation to a given quantity of cells, leads to a 50% inhibition of the paf or lyso paf binding.

The procedure of the present invention in which down-regulation of eosinophil receptors by submaximal (preferably 5 and 10 nM) paf concentrations is used has been tested successfully, for example, with a hydrophilic triazolothienodiazepine. Antagonists can be preferably tested in screening procedure according to the present invention using freshly prepared cells, leukocytes in culture or various cell lines.

According to the invention, monoclonal or polyclonal antibodies can be formed against ether phospholipids and their receptors preferably in labeled, coloured or fluorescent form. Ligands bound preferably to neutrophil or eosinophil receptors can be used for simple and quick diagnostic clinical tests for indicated disorders (for example, microscopical analysis) preferably in a coloured or fluorescent form. This is suitable as the volume of blood which is necessary to prepare, for example, blood eosinophils is very high. Finally, paf receptors on the surface of intact cells are stable for five days in special testing containers and thus the receptor status of blood cells can be investigated in central institutes when blood is taken into special testing containers which should be commercial available and which should be modified for smaller blood volumes as proposed in German utility model application G 87 16 004.8.

Since the specific binding of paf or paf-like compounds is closely related to the cellular effects particularly cellular calcium stream, the procedure of the present invention can also be used for measuring the effect of paf or paf like compounds on leukocytes by comparing their effect on the cellular calcium stream with calibration graphs of synthetic paf.

The following examples serve to explain the invention more clearly:

EXAMPLE 1

Lyso Paf in the Cerebrospinal Fluid of Patients With Psychiatric Disorders

Summary

Phospholipids were extracted from the cerebrospinal fluids of patients (n=48) with mental and inflammatory disorders. Quite surprisingly, an elevated level of lyso paf was found in the fluids of patients with psychosis and inflammatory neuronal diseases, particularly in the acute phase of multiple sclerosis. Lyso paf per 500 µl cerebrospinal fluid and lyso paf per mg albumin was significantly higher, for example, in cases of psychosis as compared with patients without psychiatric symptoms ($p<0.013$ and $p<0.03$). In contrast, paf was not detected in the probes of cerebrospinal fluids. The amounts of the paf precursor and metabolite lyso paf were analysed, for example, by HPLC analysis and tested using aspirinated CP/CPK treated platelets of rabbits as described [J. Benveniste, C. R. Acad. Science (Paris), 289:1037 (1979)] (herein incorporated by reference). Values were given with coded patient numbers (values are means±s.d. of indicated patient numbers) with no values for number 7 and 43–48 (n=7).

1.1 Elevated Lyso Paf Level in Psychosis

No. 18) Organic psychosis. 3.87 ng/500 µl, 0,043 mg albumin, 90.0 ng/mg albumin.
No. 26) Disorientated psychosis. 9.0 ng/500 µl, 0.0875 mg albumin, 102.8 ng/mg albumin.
No. 37) Schizoaffective psychosis. 15.5 ng/500 µl, 0.206 mg albumin, 75.24 ng/mg albumin.
No. 39) DD affective/organ. psychosis. 5.73 ng/500 µl, 0.055 mg albumin, 104 ng/mg albumin.
No. 40) SDAT. 10.5 ng/500 µl, 0.077 mg albumin, 136 ng/mg albumin.

n=5, x=8.92±4.5 ng lyso paf/500 µl,
n=5, x=0.0927±0.06596 mg albumin/500 µl,
n=5, x=101.61±22.47 ng lyso paf/mg albumin

1.2 Inflammatory Diseases of the Central Nervous System Including Multiple Sclerosis No. 5) State after bite of a tick with sudden reduction of the faculty of vision (Gen. not clear, encephalitis?). 3.04 ng/500 µl, 0.0535 mg albumin, 56.82 ng/mg albumin.
No. 21) Unclear virus disease, (for exclusion of inflammatory cerebral disease). 4.41/500 µl, 0.083 mg albumin, 53.13 ng/mg albumin.
No. 30) Unclear inflammatory symptoms of the brain stem, 5,0 ng/500 µl, 0.139 mg albumin, 35.97 ng/mg albumin.
No. 29) Depress. syndrome during multiple sclerosis. 6.25 ng/500 µl, 0.139 mg albumin, 55.30 ng/mg albumin.
No. 31) Depress. syndrome during multiple sclerosis 8.5 ng/500 µl, 0.0705 mg albumin 120.6 ng/mg albumin.
No. 33) Suspicion in inflammatory cerebral disease, 3.2 ng/500 µl, 0.062 mg albumin, 51.61 ng/mg albumin.
No. 34) Control after penicillin treatment of a luetic cerebral disease, with meningitis. 3.94 ng/500 µl, 0.01035 mg albumin, 38.06 ng/mg albumin.
No. 36) Suspicion in E.d., 7.5 ng/500 µl, unknown mg albumin.
No. 41) Brain atrophy (VII, VIII, IX, XII) and encephalitis. 20.0 ng/500 µl, 0.2985 mg albumin, 67.0 ng/mg albumin.

n=9, x=6.87±5.26 ng lyso paf/500 µl,
n=8, x=0.1069 mg albumin/500 µl,
n=8, x=60.43±26.38 ng lyso paf/mg albumin

1.3 Neoplastic Disease

No. 25) Plasmoblastic lymphoma, since 3 days Oculomotoriusparesis li. 14.8 ng/500 µl, 0.2295,mg albumin, 61.0 ng/mg albumin.

1.4 Hebephrenia

No. 2) 3.04 ng/500 µl, 0.0535 mg albumin, 56.82 ng/mg albumin.
No. 3) 3.37 ng/500 µl, 0.0615 mg albumin, 54.8 ng/mg albumin.
No. 17) 4.37 ng/500 µl, 0.132 mg albumin, 33.1 ng/mg albumin.

n=3, x=3.59 ng lyso paf/500 µl,
n=3, x=0.0823±0.0432 mg albumin/500 µl,
n=3, x=48.2±13.15 ng lyso paf/mg albumin

1.5 Paranoid Syndrome

No. 6) Paranoid hallucinatory schizophrenia, DD drug-induced psychosis. 2.17 ng/500 µl, 0.049 mg albumin, 44.3 ng/mg albumin.
No. 11) Paranoid syndrome. 4.37 ng/500 µl, 0.132 mg albumin, 33.11 ng/mg albumin.
No. 14) Discrete paranoid syndrome, for exclusion of an inflammatory cerebral disease. 4.0 ng/500 µl.
No. 15) Paranoid syndrome. 3.87 ng/ 500 µl, 0.0935 mg albumin, 41.39 ng/mg albumin.
No. 35) Fluctuating paranoid symptoms, organic origin. 3.94 ng/500 µl, 0.1035 mg albumin, 38.06 ng/mg albumin.
n=5, x=3.66±0.86 ng lyso paf/500 µl,
n=4, x=0.0945±0.034 mg albumin/500 µl,
n=4, x=39.215±4.8 ng lyso paf/mg albumin

1.6 Cerebral or Neuronal Disorders of Different Origin

No. 4) Suspicion in Tolora Hunt syndrome left, 2.48 ng/500 µl, 0.089 mg albumin, 27.86 ng/mg albumin.
No. 8) Ophthalmic hospital, 2.37 ng/500 µl, 0.07 mg albumin, 33.85 ng/mg albumin.
No. 9) Compulsion neurosis, 2.35 ng/500 µl, 0.100 mg albumin, 23.5 ng/mg albumin.
No. 13) Unclear muscle atrophy. 3.75 ng/500 µl, 0.081 mg albumin, 46.29 ng/mg albumin.
No. 19) Choreal syndrome with Dyskenisie. 4.62 ng/500 µl, 0.0645 mg albumin, 71.62 ng/mg albumin.
No. 22) Opticus atrophy. 4.62 ng/500 µl, 0.0555 mg albumin, 83.24 ng/mg albumin.
No. 23) Opticus atrophy. 3.87 ng/500 µl, 0.0745 mg albumin, 51.95 ng/mg albumin.
No. 24) For exclusion of organic brain disease. 3.395 ng/500 µl, 0.1075 mg Alb, 31.58 ng/mg albumin.

n=8, x=3.43±0.95 ng lyso paf/500 µl,
n=8, x=0.07913 mg albumin/500 µl,
n=8, x=46.23±21.6 ng lyso paf/mg albumin

1.7 Without Clinical Disorders

No. 12) 1.8 ng/500 µl, 0.0575 mg albumin, 31.3 ng/mg albumin.
No. 27) 3.94 ng/500 µl, 0.1355 mg albumin, 29.08 ng/mg albumin.
No.28) 2,875 ng/500 µl, 0.1645 mg albumin, 17.48 ng/mg albumin.

n=3, x=2.87±1.0 ng/500 µl,
n=3, x=0.125±0.004 mg albumin/500 µl,
n=3, x=25.9±95 ng lyso paf/mg albumin

EXAMPLE 2

Phospholipid Receptors on Human Leukocytes

Summary

The present invention shows functionally relevant paf receptors on neutrophils and eosinophils and lyso paf receptors on neutrophils but not on eosinophils. Lyso paf and paf receptors are distinct. Differences between paf receptors on leukocytes were detected with tenfold higher eosinophil $K_d$ values as compared with neutrophils. A $K_d$ value of 5.5 nM presents firstly moderate affinity (ma) paf receptors with $8.6 \times 10^4$ sites per eosinophil and calculated $K_d$ value of neutrophils was 0.44 nM with 3612 binding sites known as high affinity (ha) paf binding sites. Metabolism of added paf occurred in the presence of intact neutrophils but not with eosinophils.

2.1 Methods

Preparation of leukocytes

According to the invention, leukocytes were prepared under sterile conditions. Neutrophils (PMN) were prepared from venous blood (40 ml) from normal donors, anticoagulated with citric acid dextrose (7:1, v/v) was sedimented for 30 to 45 min in gelatin 0.3% final (Plasmagel®). Twenty ml of supernatant were layered on 10 ml Ficoll Hypaque (d=1.077) and centrifuged (400×g, 20 min, 20° C.). The cell pellet containing PMN (95%) was resuspended in 500 µl Tyrode's buffer (pH=7.4). Erythrocyte lysis was performed by adding 3 volumes of distilled water for 40 sec, followed by 1 volume NaCl (3.5%, w/v). PMN were then washed twice in Tyrode's buffer (centrifugation at 370 x g at 20° C. for 10 min). Cell concentration was adjusted to $5 \times 10^7$ per ml.

Eosinophils were also prepared under sterile conditions. Blood (400 ml) was mixed with 10% (v/v) dextran. The supernatant was carefully deposited on a metrizoate/ficoll suspension (d=1.148) after sedimentation of red blood cells and centrifuged (400×g: 40 min). Erythrocyte lysis was performed by adding 3 v. of distilled water for 40 sec, followed by 1 v. NaCl (3.5%, w/v). Cells were suspended in 500 µl pH 7.4 Tyrode's buffer, centrifuged (1900 rpm×10 min) and resuspended ($5 \times 10^6$ cells/ml) in Tyrode's (0.25% BSA) without $Ca^{2+}$. The eosinophils fraction at $1 \times 10^6$ cells/ml contained 96±5% eosinophils, 3±3% neutrophils, 1±2% mononuclear cells and no free platelets (mean±s.d., n=3).

Binding Studies

Binding studies were performed using, for example, intact neutrophils (PMN) or intact human blood eosinophils. PMN ($2.5 \times 10^6$) or eosinophils ($2.5 \times 10^5$) were suspended in 500 µl Tyrode's buffer supplemented with 1.3 mM $CaCl_2$, 1 mM $MgCl_2$ and 0.25% (v/v) fatty acid-free bovine serum albumin (BSA, w/v) were incubated with [$^3$H]paf (0.325–6.5 nM) either for 30 min at 20° C. or for 20 hrs at 4° C. Non-specific binding was assessed with the unlabeled ligands either paf (500 nM) or the receptor antagonist WEB 2086 (1 µM or 400 nM).

In a second set of experiments, [$^3$H]paf binding was performed by adding 3.25 nM [$^3$H]paf to PMN, simultaneously with low dose (5 to 50 nM) of paf, lyso paf, the enantiomer of paf or 2-lyso phosphatidylcholine (LPC) for 30 min at 20° C. [$^3$H]paf binding was also measured in the presence of the phorbol ester 4-phorbol-12-myristate-13-acetate (PMA, 1 to 16 nM) either added simultaneously with [3H]paf or preincubated 15 min at 37° C. previously. The binding of [$^3$H]lyso paf (0.325–0.5 nM) was measured after 30 min incubation at 20° C. in the absence or presence of an excess of unlabeled lyso paf (500 nM), paf (500 nM) or WEB 2086 (1 µM). The effect of low dose paf (5 nM) on the binding of [$^3$H]lyso paf was also investigated. Eosinophils were added to Tyrode's (0.25% BSA, 1.3 mM CaCl$_2$, 1 mM MgCl$_2$) containing [$^3$H]paf (0.325–6.5 nM) in the absence or presence of unlabeled paf, lyso paf, enantio-paf or lyso-phosphatidylcholine (LPC) (5, 10, 50, 500 nM) and/or the specific paf receptor antagonist WEB 2086 (400 nM). After the binding procedure, cells were separated from their suspending medium by filtration in a millipore vacuum system with GF/C filters. Filters were washed with 10 ml Tyrode's buffer at 4° C. and radioactivity was assessed by scintillation. Cell-bound radioactivity on the filters after subtraction of blanks (filter-bound radioactivity in the absence of cells) was expressed in fmol [$^3$H]paf bound per $2.5 \times 10^6$ PMN or $2.5 \times 10^5$ eosinophils.

Measurement of Cytosolic Free Calcium

The concentration of cytosolic free calcium [Ca$^{2+}$]i was measured using the [Ca$^{2+}$]i indicator fura-2-acetoxymethyl ester (fura-2). After osmotic lysis of erythrocytes, cells were washed once, resuspended in Tyrode's buffer containing 0.25% BSA, then incubated for 30 min at 37° C. with 2.5 µM fura-2 and washed twice thereafter. They were resuspended in Tyrode's buffer (0.25% BSA) containing either 1.3 mM CaCl$_2$ or 2 mM EGTA and fluorescence changes were monitored using a spectrofluorophotometer Shimadzu RF-500 (Kyoto, Japan). Paf or lyso paf (1–100 nM) was added to PMN ($2 \times 10^7$ per ml) or eosinophils ($5 \times 10^5$ per ml) at increasing concentrations (1–100 nM) under stirring, 3 min after addition of WEB 2086 (1 µM) or vehicle (0.1% water). Cytoplasmic calcium flux was also measured in cells preincubated with 1 µM WEB 2086 for 3 min before addition of 1 to 500 nM paf. The spectrofluorophotometer was programmed to shuttle between the two excitation wavelengths of 340 and 380 nm every 5 sec while keeping the emission wavelength of 505 nm. The addition of paf produced reciprocal changes (ratios, R) in the fluorescence recorded at two wavelengths, from which [Ca$^{2+}$]i can be calculated. The maximal ratio (R$_{max}$) was obtained by adding 15 µl digitonin (4 µM) and the minimal ratio (R$_{min}$) by adding 37.5 µl EGTA (5 mM). Background values were subtracted from all data. The intracellular Ca$^{2+}$ was calculated with the formula [Ca$^{2+}$]i=k×R−R$_{min}$/R$_{max}$−R. K is KD of the fura-2 multiplied with the quotient of the fluorescence at 380 nm from the minimal and the maximal [Ca$^{2+}$]i fluorescence.

[$^3$H]paf Metabolism

Cells were incubated under binding conditions with [$^3$H]paf (0.65 to 6.5 nM) or [$^3$H]lyso paf (3.25 nM), in the absence or presence of 5 nM unlabeled paf or 1 µM WEB 2086. Cells were then separated by vacuum filtration and phospholipids were extracted. Briefly, filters were placed in 500 µl water. Dichloromethane/methanol (1:2, v/v) was added overnight at 4° C., before addition of water containing 2% (v/v) acetic acid. Organic phases were collected and aqueous phases were washed three times with 1 v dichloromethane. High pressure liquid chromatography (HPLC) was performed using standard procedure with dichloromethane/methanol/water (50:50.5, by vol) and eluted with a flow rate of 1 ml/min. The radioactivity was measured in the fractions after subtraction of the background values. Appropriate synthetic markers were used to define the retention time of alkyl-acyl-glycerophosphocholine (alkyl-acyl-GPC) as 11–13 min, paf as 8–25 min and lyso paf 28–33 min.

Materials

Tyrode's buffer was composed of (in mM) NaCl, 137; KCl, 2.68; NaCO$_3$, 11.9; MgCl$_2$, 1.0; NaH$_2$PO$_4$, 0.41; dextrose, 0.5; HEPES 5.0. The following reagents were used: ACD composed of citric acid (0.8%), trisodic citrate (2.2%) and glucose (2.45%); citric acid (0.15M) (all from Merck-Darmstadt, Germany). Fatty acid-free bovine serum albumin (BSA, fraction V) and phorbol-12-myristate-13-acetate (PMA) were from Sigma (St. Louis, Mo., U.S.A.). Radiolabeled synthetic paf-acether ([$^3$H]paf, 1-O-[$^3$H]-octadecyl-2-acetyl-sn-glycero-3-phosphocholine, 80 Ci/mmol) and labeled lysopaf ([$^3$H]lyso-paf, [$^3$H]paf, 1-O-[$^3$H]-octadecyl-sn-glycero-3-phosphocholine, 150 Ci/mmol) as well as PCS and OCS scintillation fluid were from Amersham (Amersham, U.K.) and were dissolved in pure ethanol. Unlabeled synthetic paf (1-octadecyl-2-acetyl-sn-glycero-3-phosphocholine) and its enantiomer as well as lyso paf (1-octadecyl-Sn-glycero-3-phosphocholine) and2-1-ysophosphocholine (LPC) were from Bachem, (Bubendorf, Switzerland) and solubilized in ethanol. WEB 2086 was solubilized ultrasonically in water with 0.1 N HCL before use. Whatman GF/C filters were from Ferrière, France. The Millipore vacuum system was from Molsheim and Fura-2AM from Calbiochem (Germany).

2.2 Results

[$^3$H]paf Bindinq to Leukocytes, For Example, Neutrophils

Intact human neutrophils (PMN) bound [$^3$H]paf in a concentration-dependent manner. Excess unlabeled paf (500 nM) or the paf receptor antagonist WEB 2086 (1 µM) inhibited [$^3$H]paf binding. The total binding of [$^3$H]paf was higher at 20° C. vs. 4° C. (310.5±13.0 vs. 157.0±27.4 fmol per $2.5 \times 10^6$ cells). The calculated K$_d$ value of neutrophils was 0.44 nM with 3612 binding sites showing high affinity (ha) binding sites at 4° C. Quite surprisingly, the specific binding remained unsaturated at 20° C. (not at 4° C.) indicating homologous receptor regulation.

Effects of Ether Phospholipids Such as Paf or Lyso Paf

As specific paf binding remained unsaturated at 20° C. we hypothesized a self triggering effect of low ligand concentrations (Table 1). Indeed, the total binding of [$^3$H]paf to PMN increased significantly in the presence of low dose unlabeled paf (5 nM, p<0.001, Student's t test for paired samples, n=6, and Table 1). The paf effect was inhibited in the presence of WEB 2086 (p<0.001, n=6). Lyso-paf (5 nM) also increased the [$^3$H]paf binding (Table 1, p<0.001, n=6). The effects of paf or lyso paf were maximal at 5 nM for 30 min incubation and increased neither with higher concentrations nor with longer incubation periods of up to 2 hrs (not shown). No additive effects on the [³H]paf binding to PMN were observed when paf and lyso paf at low concentration were incubated together (not shown), suggesting that the common ether group in the sn-1 position of both molecules is critical for this receptor up-regulation. This was further evidenced by the fact that neither the paf enantiomer nor the ester group in the sn-1 position of LPC showed an up-regulatory effect on [³H]paf binding (Table 1).

[³H]lyso Paf Binding to Neutrophils

To strengthen the hypothesis that there are distinct binding sites for paf and lyso paf in the neutrophil membrane, we investigated the [³H]lyso paf binding. As well as binding [³H]paf, PMN bound [³H]lyso paf in a concentration-dependent manner at 20° C., but neither paf (500 nM) (FIG. 1) nor the paf receptor antagonist WEB 2086 inhibited labeled lyso paf binding (not shown). In contrast, the [³H]lyso paf binding increased in the presence of 500 nM unlabeled paf. This prompted us to confirm whether low concentrations of paf could have the same effect. Indeed, paf (5 nM) increased the binding of 3.25 nM [³H]lyso paf from 197.0±4.5 to 255.0±10.5 fmol per $2.5 \times 10^6$ PMN (n=3). The paf (not lyso paf) effect was prevented by the paf receptor antagonist WEB 2086 (1 µM, 212.0±6.4 fmol/$2.5 \times 10^6$ PMN). Unlabeled lyso paf inhibited [³H]lyso paf binding, although this inhibitory effect did not reach saturation at 20° C. (but at 4° C., not shown). These results might indicate two binding sites, the first with the ability to bind the ether group present in lyso paf with upregulatory potency, the second one with the ability to bind the acetyl group of paf.

Effect of PKC Activation on Paf Receptors

We suspected a direct interaction of ether phospholipids with protein kinase C (PKC) to regulate paf and lyso paf receptors. Indeed, an up- and down-regulatory effect was observed depending just as the effect of paf, on the concentration of the PKC activator PMA (Table 2). Low concentration of PMA (1 nM) increased [3H]paf binding, at a level similar to that of 5 nM paf and a higher concentration (16 nM) was inhibitory showing an intermediate of protein kinase C activation for receptor regulation. Preincubation of PMN with PMA for 15 min at 37° C. enhanced the dual PMA effect with up-regulation at low and down-regulation at high concentrations. Pretreatment with low dose paf desensitized PMN against a second paf challenge and thus failed to up-regulate paf receptors. No homologous paf receptor regulation was found after preincubation of PMN for 15 min at 37° C.

Specific [³H]paf Binding to Eosinophils

Eosinophils bound [³H]paf in a concentration-dependent manner after 20 hrs incubation at 4° C. The specific [³H]paf binding assessed either with unlabeled paf (500 nM, FIG. 2 A) or the specific paf receptor antagonist WEB 2086 (400 nM, Figure. 2 B) reached similar maximal plateau values (14.0±9.0 and 14.8±5.1 fmol per $2.5 \times 10^5$ cells) at concentrations higher than 3.25 nM added [³H]paf. The binding affinity (Kd) was 5.5 nM with $B_{max}$ of 35.4 fmol per $2.5 \times 10^5$ cells, corresponding to $85 \times 10^3$ binding sites per eosinophil showing moderate (ma) affinity paf receptors. However, at 20° C. (30 min, n=6), we encountered 2 different cell populations. In 3 experiments specific [³H]paf binding, verified with WEB 2086 (400 nM), reached plateau values (25.8±8.1 fmol) whereas in 3 other experiments no inhibitory effect of WEB 2086 was observed (4.3±3.3 fmol) indicating down-regulation of hetrazepine binding sites. No additive inhibitory effects on [³H]paf binding were found when both WEB 2086 (400 nM) and unlabeled paf (50 to 500 nM) were added together neither at 4° C. nor at 20° C. (Table 3). Lyso paf, enantio paf and LPC (not shown) did not interfere with [³H]paf binding.

As inefficiency of WEB 2086 in 3 of 6 experiments at 20° C. could be attributed to a down-regulation of paf receptors we investigated the effect of low dose paf on WEB 2086 efficacy. Indeed, submaximal dose of unlabeled paf (*5 and *10 nM, not 50 and 500 nM) decreased the inhibitory effect of WEB 2086 on [³H]paf binding in a significant manner (Table 3, ,p<0.01, using the "Mann Whitney" test, n=8). These phenomena were specific as lyso paf, the enantio-paf or LPC were unable to modulate the effect of WEB 2086.

Cytoplasmic Ca²⁺ Flux

In an attempt to investigate whether paf and lyso paf binding sites are causatively involved in the cellular Ca²⁺ flux, we measured the cytoplasmic Ca²⁺ changes in response to paf (FIG. 3 A, B) in comparison with lyso paf. Addition of paf (1 to 500 nM) to fura-2 loaded neutrophils in the presence of extracellular $CaCl_2$ (1.3 mM) induced a concentration-dependent entry of Ca²⁺. PMN preincubation (3 min) with WEB 2086 (1 µM) shifted to the right the paf dose-response curve. Similarly, when PMN were suspended in a medium devoid of $CaCl_2$ in the presence of EGTA (2 mM), paf induced the cytosolic mobilization of Ca²⁺ from internal pools. WEB 2086 competed with paf receptors as it shifted to the right the paf dose-response curve in a parallel manner.

In contrast, lyso paf induced neither [Ca²⁺]i entry nor mobilization (not shown). Even when PMN were incubated with 5 nM paf together with increasing concentrations of lyso paf, no additional increase of [Ca²⁺]i could be observed. These results show the requirement of the acetyl group in sn-2 position of paf for the paf (not lyso paf) receptor-dependent cellular [Ca²⁺]i mobilization.

The function of paf receptors on intact human eosinophils was explored by monitoring [Ca²⁺]i rise in response to paf. Addition of paf (1–100 nM) to fura-2-loaded eosinophils in a Ca²⁺ free buffer in the presence of EGTA (2 mM) produced a concentration-dependent elevation of [Ca²⁺]i (FIG. 4). WEB 2086 competitively inhibited the paf-mediated [Ca²⁺]i rise as it shifted to the right the dose-response curve in a parallel manner.

Paf Metabolism

The metabolism of [³H]paf to alkyl-acyl-GPC with lyso paf as an intermediary was shown under binding conditions (Table 4). Intact eosinophils did not metabolize added paf (data not shown).

2.3 Legends and Tables

Figure 1

[³H]lyso paf binding to human neutrophils

PMN ($2.5 \times 10^6$ per 500 µl) were incubated with indicated concentrations of [³H]lyso paf (at 20° C.) before vacuum filtration after 30 min incubation period. The total [³H]lyso paf binding (●) increased in the presence of unlabeled paf (500 nM, □). The non-specific lyso paf binding (○) was assessed with excess unlabeled lyso paf (500 nM) and the difference between total and non-specific binding was calculated (■). Results are means ±SEM of 3 experiments. FIG. 1 shows lyso paf receptors on neutrophils.

Figure 2

[³H]paf binding to intact human eosinophils

Eosinophils ($2.5 \times 10^5$ per 500 μl) were incubated in the presence of [³H]paf concentrations as shown for 20 hrs at 4° C. before vacuum filtration. Non-specific binding was assessed with 500 nM unlabeled paf (A, ○) or the specific paf receptor antagonist 400 nM WEB 2086 (B, □). The specific binding (■) was calculated as total (●) minus non-specific binding. Values are means±1 s.d. of 6 experiments. FIG. 2 shows moderate affinity (ma) paf receptors on intact human eosinophils.

Figure 3

Paf dose response curve of the cytosolic $Ca^{2+}$ flux in PMN

PMN (106 per ml) were incubated for 3 min at 37° C. under stirring with WEB 2086 (○) or vehicle (●) before paf was added at indicated concentrations in the presence of $CaCl_2$ (A) or in the same buffer devoid of $CaCl_2$, containing EGTA (B). Means±1 s.d. are of 3 experiments. Cytosolic $Ca^{2+}$ flux in PMN depends on the acetyl group present in paf (not lyso paf).

Figure 4

Paf dose-response curve of the cytosolic $Ca^{2+}$ flux

Eosinophils (105 per ml) were incubated for 3 min at 37° C. under stirring with WEB 2086 (□) or vehicle (●) before paf was added at indicated concentrations in a buffer devoid of $CaCl_2$, containing 2 mMEGTA. Values are means±1 s. d. of 3 experiments. FIG. 4 shows functional relevant (ma) paf receptors on human eosinophils.

30 min, $2.5 \times 10^6$ PMN) reaching plateau values at 5 nM. WEB 2086 (1 μM) inhibited increased [³H]paf binding. Table 1 shows that lyso paf receptors on PMN are functionally relevant.

TABLE 2

| Effect of PMA on the [³H]paf binding | | | | |
|---|---|---|---|---|
| Preincubations: | | | paf | PMA (nM) |
| (min at 37° C.) | none | paf 5 (nM) | +WEB 2086 | 1 | 16 |
| 0 | 354 | 414 | 274 | 385 | 219 |
| 15 | 342 | 331 | 226 | 413 | 171 |

Dual effects of paf and PMA were found when added with [³H]paf simultaneously (3.25 nM, 30 min, 20° C.). The dual effect of PMA (not paf) increased after 15 min preincubation. Results are expressed in fmol [³H]paf bound per $2.5 \times 10^6$ PMN and are representative of 6 experiments. Table 2 shows that the direct PKC activation with PMA modulates paf receptors on PMN.

TABLE 1

| | Increase of [³H]paf binding by ether phospholipids | | | | | |
|---|---|---|---|---|---|---|
| Add. (nM) | paf | paf +WEB | lyso paf | lyso paf +WEB | enantio- paf | LPC |
| 0 | 318 ± 15[1)] | — | — | 348 ± 17 | 348 ± 17 | — |
| 5 | 376 ± 21* | 258 ± 19* | 354 ± 20* | 257 ± 19* | 345 ± 32 | 322 ± 22 |
| 10 | — | 346 ± 20* | 243 ± 16* | 343 ± 29 | 310 ± 19 | — |
| 50 | — | 342 ± 19* | 240 ± 18* | 325 ± 25 | 311 ± 19 | — |

Values are means±1 S.E.M. of six experiments with significant, effects ($p<0.001$ vs control[t]) "Student's t test for paired samples". The control is the total binding without addition of the antagonist or the unlabeled agonist.

[³H]paf binding increased at indicated dose of paf or lyso paf, but not paf enantiomer and lyso phosphatidylcholine (LPC). Lyso paf increased [³H]paf binding (3.25 nM, 20° C.,

TABLE 3

| | Homologous down-regulation of eosinophil paf receptors | | | |
|---|---|---|---|---|
| Addition of paf (nM) | paf | WEB 2086 +paf (n = 8) | lyso paf (n = 3) | WEB 2086 +lyso paf (n = 3) |
| 0 | — | 15.1 ± 8.0[1)] | — | — |
| 5 | 3.8 ± 5.0 (n = 4) | *7.1 ± 5.0 | 1.5 ± 1.7 | — |
| 10 | 4.3 ± 2.9 (n = 5) | *2.3 ± 2.9 | 1.2 ± 1.6 | 14.3 ± 6.9 |
| 50 | 7.2 ± 5.4 (n = 8) | 18.4 ± 11.8 | 4.4 ± 3.7 | 14.9 ± 7.5 |
| 500 | 12.5 ± 6.9 (n = 4) | — | — | — |

Values are calculated as fmol per $2.5 \times 10^5$ cells and are means±1 s.d., where n=the number of experiments. Effects were significant vs. control[1] (p<0.01, "Mann Whitney" test).

The specific [$^3$H]paf binding decreased in the presence of indicated low concentrations of unlabeled paf. Submaximal paf decreased significantly* the inhibitory effect of WEB 2086 (400 nM, 20° C., 30 min). Neither lyso paf, LPC nor enantio paf interfered with [$^3$H]paf binding. Table 3 shows down-regulation of paf receptors on eosinophils.

TABLE 4

| | Cellular metabolism of [$^3$H]paf | | |
|---|---|---|---|
| Addition | paf | lyso paf | alkyl-acyl-GPC |
| control | 80.0 ± 10.8 | 1.3 ± 1.2 | 8.1 ± 11.6 |
| paf (5 nM) | 78.9 ± 11.3 | 0.8 ± 0.8 | 22.1 ± 11.9 |
| WEB 2086 | 82.3 ± 8.0 | 0.5 ± 0.8 | 16.7 ± 8.5 |

PMN ($2.5 \times 10^6$) metabolized added [$^3$H]paf to [$^3$H]alkyl-acyl-GPC and [$^3$H]lyso paf as an intermediary. PMN were incubated with [$^3$H]paf under functionally relevant binding conditions (6.5 nM, 30 min at 20° C.) before separation by filtration. PMN-bound phospholipids on filters were extracted and purified by HPLC. Values are expressed as a percentage of radioactivity recovered in all fractions after subtraction of the background values. Means ±1 s.d. are from 3 experiments.. Table 4 shows that low dose paf increased slightly the paf metabolism in PMN (not in eosinophils).

EXAMPLE 3

Acetylhydrolase Release From Platelets

Summary

Platelets release paf degrading acetylhydrolase during aggregation and this effect can be inhibited by serum albumin.

3.1 Methods

All methods were described by Korth et al. [Lipids, 28: 193–199 (1993) and Eur. J. Pharmacol., 152:101 (1988)]. Results are expressed as mean±S.D. or S.E. and statistics were performed using the "Mann Whitney" test (n=3, n=5 or n=6 as indicated).

3.2 Results

Inhibitory Effect of Serum Albumin

Paf was not metabolized during platelet aggregation in response to low concentrations of paf (0.1 to 5 nM). Serum albumin (BSA, 0.25%) inhibited paf-mediated platelet aggregation: $EC_{50}$ values increased to 0.4±0.1 and 0.9±0.2 nM paf after 3 min aggregation with a maximal aggregation at 2.6±0.5 and 5.0±0.5 nM paf at 20° C. and 37° C., respectively. Platelets degraded [$^3$H]octadecyl paf in parallel with LDH release in the supernatants (cell damage). Serum albumin protected platelets (Table 5).

Release of Acetylhydrolase During Platelet Aggregation

Platelets released acetylhydrolase during aggregation in response to thrombin and high dose paf in a time-dependent manner (Table 6). No increase in LDH release was observed (1.5%, n=2). Unstimulated platelets did not release acetylhydrolase. Thrombin (0.5 IU/ml) or high concentrations of paf (500 nM) released 17.2±3.1% and 10.3±1.5% (mean±S.E., n=3) of the total acetylhydrolase, respectively. When platelets were incubated for 30 min (37° C.) at pH 9.5, 14.7±4.9% and 37.5±2.5% of acetylhydrolase and LDH were respectively released (mean±S.E., n=3). These data indicate that the releasable pool of the acetylhydrolase is limited.

Kinetic Studies of Acetylhydrolase

The acetylhydrolase activity was measured in plasma, in cell lysates (cells and supernatants) from non-activated and thrombin-activated platelets and in supernatants from thrombin-activated platelets (Table 7). The acetylhydrolase activity in all preparations was linear with the time of incubation through at least 10 min and with the protein concentration up to 100 µg/ml (data not shown). Under these conditions [$^3$H]acetate release from [$^3$H]acetyl paf reached nearly a plateau at 20–40 µM. The acetylhydrolase activity was independent of the presence of $Ca^{2+}$ in the assay, and was not inhibited by excess AAGPC (1-Q-hexadecyl-2-palmitoyl-GPC, data not shown), suggesting that the activity was not the classical phospholipase $A_2$ type.

The affinity of the acetylhydrolase for paf ($K_m$ values) was calculated from the Lineweaver Burk plot (not shown). The statistical analysis of the data showed a significant difference of the $K_m$ values (Table 7) when measured in the supernatants of thrombin-activated platelets as compared to lysed platelets and to plasma (n=5, p<0.05). The release of acetylhydrolase from activated platelets decreased the $K_m$ value similar to that found in the plasma suggesting that the microenvironment modifies the plasma enzyme which originates from activated platelets.

The $v_{max}$ values for acetylhydrolase are shown in Table 7. These values were calculated in relation to the total protein content of the assay (not shown) and not to the pure acetylhydrolase protein. Thus, they reflect the relative enrichment in acetylhydrolase of the supernatants obtained from activated platelets in comparison to cell lysate leading to extracellular lyso paf production.

3.3 Tables and Legends

TABLE 5

| Paf Metabolism by Resting or Activated Platelets | | | |
|---|---|---|---|
| Treatment of platelets | LDH (% release) | Lyso paf (%) | Alkylacyl-GPC |
| (1) BSA, pH 7.4 | 4.6 ± 0.4 (3) | 0.7 ± 0.7 | 1.5 ± 0.8 (3) |
| (2) pH 7.4 | 9.0 (2) | 3.5 ± 0.6 | 4.5 ± 1.8 (4) |
| (3) BSA, pH 9.5 | 13.0 (2) | 10 | 0 (1) |
| (4) pH 9.5 | 20.5 ± 5.7 | 5.7 ± 3 (4) | — |

TABLE 5-continued

Paf Metabolism by Resting or Activated Platelets

| Treatment of platelets | LDH (% release) | Lyso paf (%) | Alkylacyl-GPC |
|---|---|---|---|
| (5) Supernatants of 4 | 37.5 ± 2.5 (3) | 20.1 ± 1.0 (3) | 2.7 ± 1.3 (3) |
| (6) Supernatants of thrombin-activated | 6.5 ± 1.5 (3) | 29.0 | 2.2 (2) |

Treated or untreated platelets or their supernatants were incubated with [$^3$H]octadecyl paf (15 nCi, 0.65 nM for 30 min at 37° C.). Labeled phospholipids were extracted and analyzed as described before. Results are in percentage of total counts (22 ±900 dpm) are mean±S.E. of (n) independent experiments. Table 5 shows release of acetylhydrolase from activated or damaged platelets with or without protective serum albumin (3 vs. 4, 5).

TABLE 6

Time-Course of Acetylhydrolase Release

| Stimulation (sec): | Paf (500 nM) | Thrombin (0.5 IU/ml) |
|---|---|---|
| 0 | 1.0 ± 1.0 | 2.2 ± 0.9 |
| 15 | 8.2 ± 3.2 | 8.5 ± 0.7 |
| 30 | 7.8 ± 2.6 | 13.1 ± 3.9 |
| 60 | 9.5 ± 4.0 | 12.8 ± 5.1 |
| 120 | 10.0 ± 1.4 | 10.9 ± 3.1 |
| 180 | 12.6 ± 3.8 | 17.9 ± 2.6 |
| 300 | 10.3 ± 1.5 | 17.2 ± 3.1 |

Results show a time dependent release of acetylhydrolase from paf- and thrombin-activated human platelets. Values are expressed in percentage of the total content of acetylhydrolase and are means±1 s.d. of three experiments.

TABLE 7

Kinetic Constants of Acetylhydrolase

| Source of acetylhydrolase | $K_m$ (μM) | $V_{max}$ (nmol/min/mg prot.) |
|---|---|---|
| (1) Platelets | 8.3 ± 1.5 | 0.3 |
| (2) Thrombin-activated platelets | 10.6 ± 1.5 | 0.3 |
| (3) Supernatant from (2) | 7.9 ± 1.5* | 1.4 |
| (4) Native plasma | 5.3 ± 0.5** | 1.4 |

Values showed significant differences in a "Mann Whitney" test (3 vs. 2 and 3 vs. 4, p<0.05; 4 vs. 1: **p<0,003; n.s.: 2 vs. 1). Results are mean±S.D. of 5 separate experiments.

Acetylhydrolase activity was measured in lysates of resting platelets or platelets stimulated with thrombin (0.5 IU/ml, 1 min, 37° C.), in supernatants of thrombin-activated platelets with or without acid-treated (inactivation of acetylhydrolase) plasma and in native plasma. Samples were incubated for 10 min at 37° C. in the presence of 0.1 ° C.i [$^3$H]acetyl paf and concentrations of unlabeled paf varying from 5 to 35 μM. The microenvironment modulates the acetylhydrolase indicating the origin of plasma acetylhydrolase from activated platelets.

EXAMPLE 4

Cholesterol and Cellular cAMP Level

Summary

Cholesterol modulates the cellular cAMP level to differentiate monocytes expressing genes of paf or lyso paf receptors. Cell differentiation interferes with aging and death of cells.

4.1 Methods

U 937 cells were grown in stationary suspension culture in RPMI 1640 containing 10% fetal calf serum (FCS) and 2 mM L-glutamine at 37° C. in a humidified atmosphere of 5% $CO_2$ and 95% air. The cells were diluted with fresh medium (1/10, v/v) twice a week. After three days in culture, U 937 cells were centrifuged (1000×G for 10 min) and incubated for 24 hrs in RPMI 1640 medium containing 10% CPSR 1 (delipidated FCS) and 2 mM L-glutamine. Subsequently the cells were incubated in the delipidated FCS medium containing cholesterol (10–60 μg/ml), as compared with solvent alone (ethanol, 0.5% v/v, final concentration) for (2, 4 or 24 hrs).

Cyclic AMP in supernatants from cholesterol-treated and control cells, were measured by the Rianen [$^{25}$I]cAMP-RIA Kit. Briefly, cholesterol (60 μg/ml, 24 hrs) or cholesterol vehicle (ethanol) were added after 24 hrs cell incubation in delipidated FCS medium. Cells were subsequently washed three times and resuspended (5×10$^6$, final concentration) in Hanks Hepes (HH)-buffer, pH 7.4 with ascorbinic acid (10 mM) and cAMP-phosphodiesterase inhibitor IBMX (1 mM). Cell suspension (100 μl) was added to 400 μl of the cAMP buffer for 30 min at 20° C. The reaction was started with increasing concentrations of paf with and without WEB 2086 (1 μM) and stopped in an ice bath after 5 min incubation at 37° C. Proteins were heat-denaturated (100° C., 5 min) and cell debris was centrifuged (5 min with 1500×G, 20° C.). Values are from one experiment (representative of three) expressed as pmol cAMP per 10$^6$ cells. Total proteins were measured by standard procedure.

Materials were obtained as indicated. U 937 cells were from ATCC (U.S.A.), RPMI 1640 culture medium, fetal calf serum and L-glutamine were from Serva (Heidelberg, F. R. G.). The delipidated fetal calf serum CPSR 1, isobutyl-1-methylxanthine (IBMX), IoA and essentially fatty-acid-free bovine serum albumin (BSA, fraction V) were from Sigma (St. Louis, Mo., U.S.A.). The RIANEN [$^{125}$I] cAMP Radio-immunoassay (RIA) Kit for cyclic adenosine monophosphate was from Du Pont Company (Billerica, Mass., U.S.A.). WEB 2086 was dissolved and sonicated in distilled water with 0.1M HCL. Ascorbic acid was from Merck (Darmstadt). Hanks Hepes buffer (HH-buffer) was from Biochem A. G. and HBSS buffer from Biochem A. G. (Germany). Tyrode's buffer contained 137 mM NaCl, 2.68 mM KCl, 11.9 mM NaHCO$_3$, 1.0 mM MgCl$_2$, 0.41 mM NaH$_2$PO$_4$, 0.5 mM dextrose, 5 mM Hepes (pH 7.4).

4.2 Results

Cholesterol Treatment and cAMP Levels of U 937 Cells

Cholesterol increased the release of cAMP levels from monocyte/macrophage like U 937 cells. Paf showed a dose dependent fall in cAMP which was partly inhibited by a paf receptor antagonist. A cholesterol-mediated receptor expression in monocytes has been described before (R. Korth, U.S. patent application Ser. No. 07/845,088).

4.3 Legend

Figure 5

Paf dose response curve for cAMP synthesis

The cAMP levels in monocyte/macrophage like U 937 cells in response to paf were measured in the presence (○ ◊) and absence (● ◆) of WEB 2086 (1 μM). Cells were incubated before in the presence of cholesterol (60 μg/ml, 24 hrs, ●○) as compared with control cells (◆ ◊). Values are expressed as pmol cAMP per 1×10$^6$ U 937 cells (means±1 s.d., n=3).

All references disclosed herein are hereby specifically incorporated by reference.

We claim:

1. A method of treating skin diseases selected from the group consisting of sclerotic, genetic and thermic disease, comprising administering to a subject requiring said treatment an effective amount of a natural ginkgolide selected from the group consisting of BN 52020, BN 52021, BN 52022 and mixtures thereof.

2. The method according to claim 1, wherein the ginkgolide is administered in a food.

3. A method according to claim 1, wherein the ginkgolide is administered topically.

* * * * *

UNITED STATES PATENT AND TRADEMARK OFFICE
CERTIFICATE OF CORRECTION

PATENT NO. : 5,605,927
DATED : February 25, 1997
INVENTOR(S) : Korth

Page 1 of 4

It is certified that error appears in the above-identified patent and that said Letters Patent is hereby corrected as shown below:

On the title page:

Item [63], line 3, delete "abandoned"

Column 3, line 34, delete "[3H]" and insert therefor -- [$^3$H] --.

Column 3, line 65, and Column 4, line 1, delete "7a-Epoxy-methano)-1H" and insert therefor -- 7a-(Epoxymethano)-1H.

Column 6, line 1, delete " SD-2 " and insert therefor -- sn-2 --.

Column 12, line 31, delete " (1-octadecyl-Sn-glycero-3-phosphocholine) " and insert therefor -- (1-octadecyl-sn-glycero-3-phosphocholine) --.

Column 12, line 31, delete " 2-1-ysophosphocholine " and insert therefor -- 2-lysophosphocholine --.

UNITED STATES PATENT AND TRADEMARK OFFICE
CERTIFICATE OF CORRECTION

PATENT NO. : 5,605,927
DATED : February 25, 1997
INVENTOR(S) : Korth

It is certified that error appears in the above-identified patent and that said Letters Patent is hereby corrected as shown below:

Column 12, line 34, delete " Ferriére " and insert therefor -- Ferrière --.

Column 13, line 39, delete "[3H]" and insert therefor -- $[^3H]$ --.

Column 15, line 18, delete " (106 per ml) " and insert therefor -- ($10^6$ per ml) --.

Column 15, line 32, delete " 2 mMEGTA. " and insert there for -- 2 mM EGTA --.

Column 16, Table 2, delete "5(nM) " and insert therefor -- (5 nM) --.

Column 19, line 62, delete " C.i " and insert therefor -- $\mu$Ci --.

UNITED STATES PATENT AND TRADEMARK OFFICE
CERTIFICATE OF CORRECTION

PATENT NO.  : 5,605,927
DATED       : February 25, 1997
INVENTOR(S) : Korth

It is certified that error appears in the above-identified patent and that said Letters Patent is hereby corrected as shown below:

Column 3, lines 56-57, delete " rac-3-(N-n-octadecyl carbamoyl oxy)-2-methoxypropyl 2-tiazolioethyl phosphate; " and insert therefor -- 3-(N-n-octadecyl-carbamoyloxy)-2-methoxypropyl-2-tiazolioethylphosphate; --.

Column 3, lines 65-66, delete " 6aH-cyclopenta(c)furo (2, 3-b) furo(3',2': 3,4) cyclopenta (1,2-d) " and insert therefor -- 6aH-cyclopenta[c]furo[2, 3-b] furo-[3', 2': 3,4] cyclopenta [1, 2-d] --.

Column 4, lines 2-3, delete " 6aH-cyclopenta(c)furo (2, 3-b) furo(3',2': 3,4) cyclopenta (1,2-d) " and insert therefor -- 6aH-cyclopenta[c]furo[2, 3-b] furo-[3', 2': 3,4] cyclopenta [1, 2-d] --.

Column 4, line 4, delete " 4b-11-trihydroxy-8-methyl; " and insert therefor -- 7b-11-trihydroxy-8-methyl; --.

UNITED STATES PATENT AND TRADEMARK OFFICE
CERTIFICATE OF CORRECTION

PATENT NO. : 5,605,927
DATED : February 25, 1997
INVENTOR(S) : Korth

It is certified that error appears in the above-identified patent and that said Letters Patent is hereby corrected as shown below:

Column 4, line 6, delete " 6aH-cyclopenta(c)furo (3',2': 3,4) cyclopenta (1,2-d) " and insert therefor -- 6aH-cyclopenta[c]furo[2, 3-b] furo-[3', 2': 3,4] cyclopenta [1, 2-d] --.

Column 4, lines 9-10, delete "(dimethoxy-3, 4-phenyl)thio)methylthiocarbonyl-9 pyrido (4',3'-4,5) thieno (3,2-f) triazolo-1,2,4 (4, 3-a) diazepine-1,4). " and insert therefor -- [(dimethoxy-3, 4-phenyl) thio] methyl-thiocarbonyl-9 pyrido[4',3'-4,5]thieno[3,2]triazolo-1,2,4[4, 3-a] diazepine-1,4. --.

Signed and Sealed this

Thirty-first Day of March, 1998

Attest:

BRUCE LEHMAN

Attesting Officer

Commissioner of Patents and Trademarks